(12) United States Patent
Barrett et al.

(10) Patent No.: US 10,416,122 B2
(45) Date of Patent: Sep. 17, 2019

(54) ULTRASONIC PHASED ARRAY TRANSDUCER APPARATUS FOR THE NONDESTRUCTIVE INSPECTION OF A COMPONENT UNDER TEST

(71) Applicant: WESTINGHOUSE ELECTRIC COMPANY LLC, Cranberry Township, PA (US)

(72) Inventors: Charles R. Barrett, Ooltewah, TN (US); Kevin J. Foley, Chattanooga, TN (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 155 days.

(21) Appl. No.: 15/798,803

(22) Filed: Oct. 31, 2017

(65) Prior Publication Data

US 2019/0128855 A1   May 2, 2019

(51) Int. Cl.
| | |
|---|---|
| *G01N 29/26* | (2006.01) |
| *G01N 29/04* | (2006.01) |
| *G01N 33/00* | (2006.01) |
| *G01N 29/265* | (2006.01) |
| *G01N 29/22* | (2006.01) |

(52) U.S. Cl.
CPC .......... *G01N 29/262* (2013.01); *G01N 29/043* (2013.01); *G01N 29/221* (2013.01); *G01N 29/265* (2013.01); *G01N 2033/0093* (2013.01); *G01N 2291/0289* (2013.01); *G01N 2291/105* (2013.01); *G01N 2291/106* (2013.01); *G01N 2291/267* (2013.01); *G01N 2291/2675* (2013.01)

(58) Field of Classification Search
CPC .......... G01N 2291/106; G01N 29/262; G01N 29/221; G01N 2291/2675; G01N 29/226; G01N 29/26; G01N 29/265
See application file for complete search history.

(56) References Cited

U.S. PATENT DOCUMENTS

| | | | | |
|---|---|---|---|---|
| 3,960,005 | A | * | 6/1976 | Vezina ..................... B61K 9/10 |
| | | | | 73/614 |
| 4,094,306 | A | * | 6/1978 | Kossoff ................ A61B 8/0825 |
| | | | | 128/915 |
| 4,149,420 | A | * | 4/1979 | Hutchison ................ A61B 8/00 |
| | | | | 367/7 |

(Continued)

FOREIGN PATENT DOCUMENTS

JP          2007114075 A  *  5/2007

*Primary Examiner* — David A Rogers
(74) *Attorney, Agent, or Firm* — Eckert Seamans Cherin & Mellott, LLC

(57) ABSTRACT

A phased array transducer apparatus includes a plurality of Phases Array Subassemblies (PASAs) that are arranged in three pairs in a single housing. The PASAs are each oriented at a compound angle with respect to a component under test in an environment such as a nuclear environment. The phased array transducer apparatus is carried into the environment by a tool, and the positioning of the PASAs on the phased array transducer apparatus results in the outputting of ultrasonic beams in various directions that avoids the need for the housing to be reoriented on the tool in order to complete an inspection of the object under test.

6 Claims, 5 Drawing Sheets

(56) References Cited

U.S. PATENT DOCUMENTS

| | | | | |
|---|---|---|---|---|
| 4,394,345 A * | 7/1983 | De Briere | G01N 29/223 | 376/245 |
| 4,640,291 A * | 2/1987 | 't Hoen | B06B 1/0629 | 310/334 |
| 4,868,798 A * | 9/1989 | Fasnacht, Jr. | G01N 29/223 | 367/104 |
| 5,563,346 A * | 10/1996 | Bartelt | G01S 15/8925 | 600/447 |
| 5,677,490 A * | 10/1997 | Gunther | G01N 29/043 | 73/620 |
| 7,293,461 B1 * | 11/2007 | Girndt | G01N 29/04 | 310/336 |
| 7,363,817 B2 * | 4/2008 | Bond | G01N 21/59 | 250/223 R |
| 7,975,549 B2 * | 7/2011 | Fetzer | G01N 29/2468 | 73/626 |
| 9,037,419 B2 * | 5/2015 | Na | G01N 29/0645 | 702/39 |
| 9,049,783 B2 * | 6/2015 | Teofilovic | H05K 1/0256 | |
| 9,347,918 B2 * | 5/2016 | Bond-Thorley | G01N 29/221 | |
| 9,636,133 B2 * | 5/2017 | Hall | A61B 17/320068 | |
| 9,733,219 B2 * | 8/2017 | Spencer | G01N 29/24 | |
| 9,945,817 B2 * | 4/2018 | Pember | G01N 29/0654 | |
| 10,113,993 B2 * | 10/2018 | Spencer | G01N 29/043 | |
| 2003/0177833 A1 * | 9/2003 | Venczel | G01N 29/27 | 73/622 |
| 2008/0178678 A1 * | 7/2008 | Girndt | G01N 29/04 | 73/622 |
| 2008/0314154 A1 * | 12/2008 | Fetzer | G01N 29/2468 | 73/638 |
| 2009/0165563 A1 * | 7/2009 | McGrath | G01N 29/225 | 73/644 |
| 2009/0178466 A1 * | 7/2009 | Ethridge | G01N 29/07 | 73/1.86 |
| 2011/0083512 A1 * | 4/2011 | Imbert | G01N 29/0645 | 73/622 |
| 2012/0143063 A1 * | 6/2012 | Robinson | A61B 8/00 | 600/472 |
| 2013/0247350 A1 * | 9/2013 | Specht | A61B 8/00 | 29/407.09 |
| 2014/0165730 A1 * | 6/2014 | Na | G01N 29/0645 | 73/588 |
| 2014/0352438 A1 * | 12/2014 | Scaccabarozzi | G01N 29/2437 | 73/632 |
| 2015/0013463 A1 * | 1/2015 | Georgeson | G01N 29/043 | 73/628 |
| 2015/0233869 A1 * | 8/2015 | Barrett | G01N 29/043 | 376/249 |

* cited by examiner

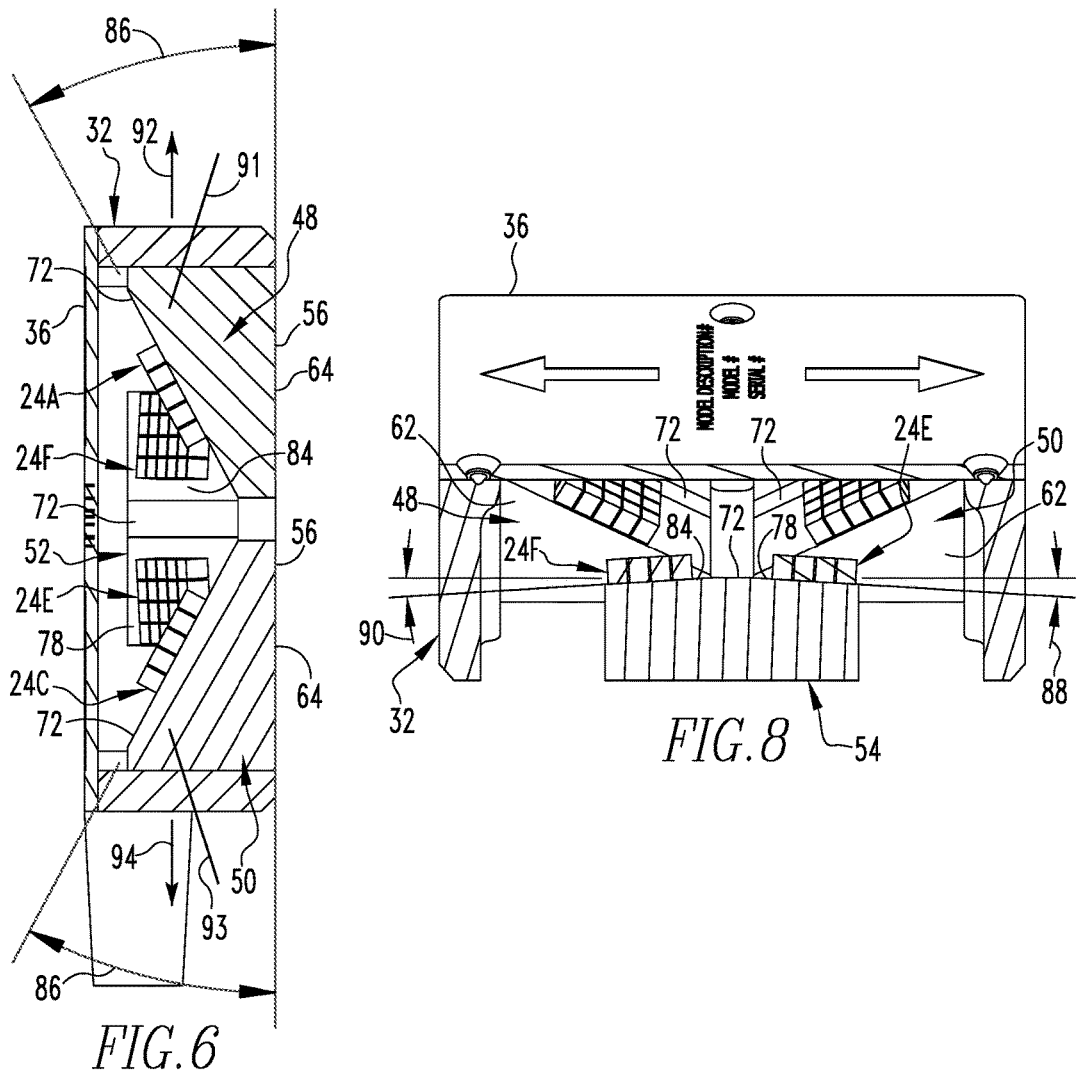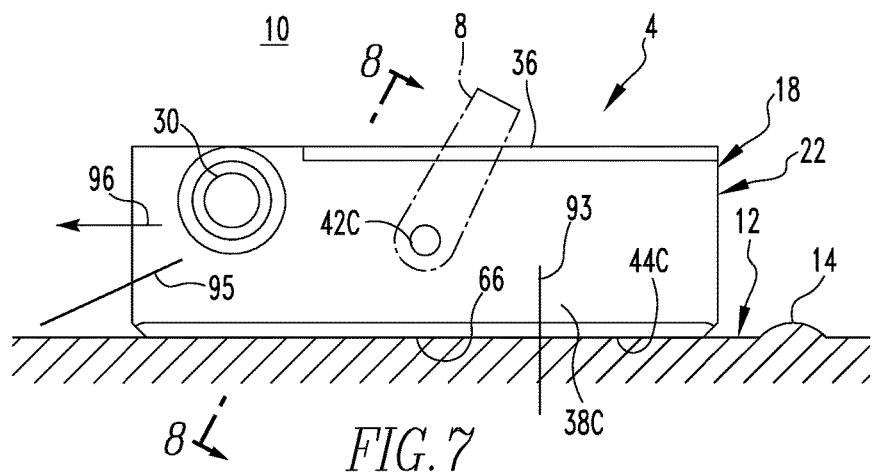

ULTRASONIC PHASED ARRAY TRANSDUCER APPARATUS FOR THE NONDESTRUCTIVE INSPECTION OF A COMPONENT UNDER TEST

BACKGROUND

1. Field

This invention relates generally to nondestructive examination transducers and, more particularly, to an ultrasonic phased array transducer apparatus for inspecting components in restricted areas, such as in a nuclear environment.

2. Related Art

A boiling water reactor (BWR) produces electrical power by heating water in a reactor pressure vessel that contains a nuclear fuel core in order to generate steam which is used to drive a steam turbine. Various components and structures in a nuclear reactor are examined periodically to assess their structural integrity and determine the need for repair. Ultrasonic inspection is a known technique for detecting cracks in nuclear reactor components. A number of the inspection areas in a nuclear environment, such as a nuclear reactor, which may include a BWR, have limited access and, therefore, are difficult to assess using an inspection tool. A shroud in a BWR is one such component.

The shroud itself and the welds formed in the shroud are periodically inspected for cracking. The presence of cracking can diminish the structural integrity of the shroud. Access to the external surface of the shroud is limited to the annular space between the outside of the shroud and the inside of the reactor pressure vessel, and between adjacent jet pumps.

Weldments including the weld and the heat affected zone adjacent the weld are ultrasonically inspected, and such region is referred to as the "weld volume." Cracking orientation typically may be circumferential (parallel to the weld), axial (perpendicular to the weld), or off-axis (i.e., neither parallel nor perpendicular to the weld). By way of example, the inspection of the weld volume for the detection of circumferential and axial orientated cracking is commonly performed by a combination of scans that involve multiple passes of a transducer or a plurality of at various rotations.

Ultrasonic (UT) testing is a method of characterizing the internal structure of a component under test through the use of high frequency sound waves. The frequencies used for ultrasonic testing are many times higher than the limit of human hearing, most commonly in the range from 500 KHz to 20 MHz. High frequency sound waves are directional, and can travel through a steel medium until the beam strikes a boundary from another medium (such as a crack or void within the component under test), at which point the beam is reflected back to be characterized.

Previous ultrasonic weldment inspection technology typically employed a single or dual element piezoelectric crystal transducer that generates a single beam and that is situated on a specified wedge-like support to create a predetermined angle in which the beam would travel through the medium. Multiple probes would be necessary to examine the weld volume in varying directions and angles, or this could be accomplished with the added complexity of remote tooling for individual transducer rotation. Phased array probes utilized for weld inspections are advantageous inasmuch as fewer transducer elements are needed and, more importantly they require less transducer manipulation. Such phased array probes employ one or more Phased Array Subassemblies (PASAs). Such PASAs have the advantage of being able to generate numerous ultrasonic beams from a single transducer assembly containing one or more rows of ultrasonic elements in which each UT element can be separately pulsed to create a single beam or multiple beams at various angles (array) in a sweeping manner in a first direction. Some phased array technology enables the transducers to steer the generated beams in a second direction without rotation of the phased array transducer. The phased array sweeping and steering capabilities are a function of the number of piezoelectric UT elements, the positioning of the UT elements within the housing, and the operations of an ultrasonic operating system that is operable on a computer and is connected with the PASAs.

Inspecting and repairing nuclear reactors, such as boiling water reactors and other reactors, typically can require complex tooling in order to position or move the phased array transducer to complete the examination. Plant utilities have a desire to reduce the number of manipulator installations and removals to reduce radiological exposure as well as cost and plant outage impact. Improvements thus would be desirable.

SUMMARY

An improved phased array transducer apparatus includes a plurality of Phases Array Subassemblies (PASAs) that are arranged in three pairs within a single housing. The PASAs are each oriented on a compound angle with respect to a component under test in an environment such as a nuclear environment. The phased array transducer apparatus is carried into the environment by a tool, and the positioning of the PASAs on the phased array transducer apparatus results in the outputting of ultrasonic beams in various directions that avoids the need for the housing to be reoriented by the tool in order to complete an inspection of the component under test.

Accordingly, an aspect of the disclosed and claimed concept is to provide a phased array transducer apparatus having six PASAs that are arranged in pairs on three wedge-like supports that are situated in a housing of the phased array transducer apparatus.

Another aspect of the disclosed and claimed concept is to provide such a phased array transducer apparatus that is carried by a tool into an environment such as a nuclear environment to enable the transducer apparatus to perform an ultrasonic inspection of a component under test.

Another aspect of the disclosed and claimed concept is to provide such a phased array transducer apparatus that can complete the ultrasonic inspection of the component under test and that avoids any need for the transducer apparatus to be repositioned on the tool (such as by requiring the tool to be removed from the environment to reposition the transducer apparatus thereon or by providing on the tool additional equipment that adjusts the position of the transducer apparatus on the tool) to enable the transducer apparatus to re-scan the same portion of the component under test in order to complete the inspection thereof.

Accordingly, an aspect of the disclosed and claimed concept is to provide an improved phased array transducer apparatus structured to be connectable with a computer and to be carried by a tool into a nuclear environment to perform an ultrasonic inspection operation on a component under test within the nuclear environment, the phased array transducer apparatus can be generally stated as including a housing that can be generally stated as including a base, the base having an engagement surface that is structured to be engaged with the component under test during at least a portion of the ultrasonic inspection operation, a plurality of Phased Array SubAssemblies (PASAs), each can be generally stated as including a plurality of ultrasonic elements and being situated on the base, the plurality of PASAs can be generally stated as including a first PASA, a second PASA, a third PASA, a fourth PASA, a fifth PASA, and a sixth PASA, the first PASA being oriented at a first oblique angle with respect to the engagement surface and being structured to output a first ultrasonic signal into the component under test, the second PASA being oriented at a second oblique angle with respect to the engagement surface and being structured to output a second ultrasonic signal into the component under test, the third PASA being oriented at a third oblique angle with respect to the engagement surface and being structured to output a third ultrasonic signal into the component under test, the fourth PASA being oriented at a fourth oblique angle with respect to the engagement surface, the fourth PASA being structured to receive from the component under test a flaw-based reflection of at least a portion of the first ultrasonic signal and to responsively generate a first output signal that is detectable by the computer, the fifth PASA being oriented at a fifth oblique angle with respect to the engagement surface, the fifth PASA being structured to receive from the component under test a flaw-based reflection of at least a portion of the second ultrasonic signal and to responsively generate a second output signal that is detectable by the computer and the sixth PASA being oriented at a sixth oblique angle with respect to the engagement surface, the sixth PASA being structured to receive from the component under test a flaw-based reflection of at least a portion of the third ultrasonic signal and to responsively generate a third output signal that is detectable by the computer

BRIEF DESCRIPTION OF THE DRAWINGS

A further understanding of the invention can be gained from the following description when read in conjunction with the accompanying drawings in which:

FIG. 6 is sectional view as taken along lines 6-6 of FIG. 5;

FIG. 7 is an end view of the phased array transducer apparatus of FIG. 1 situated on a component under test; and FIG. 8 is a sectional view as taken along line 8-8 of FIG. 7.

Similar numerals refer to similar parts throughout the specification.

DESCRIPTION

Figure 1:
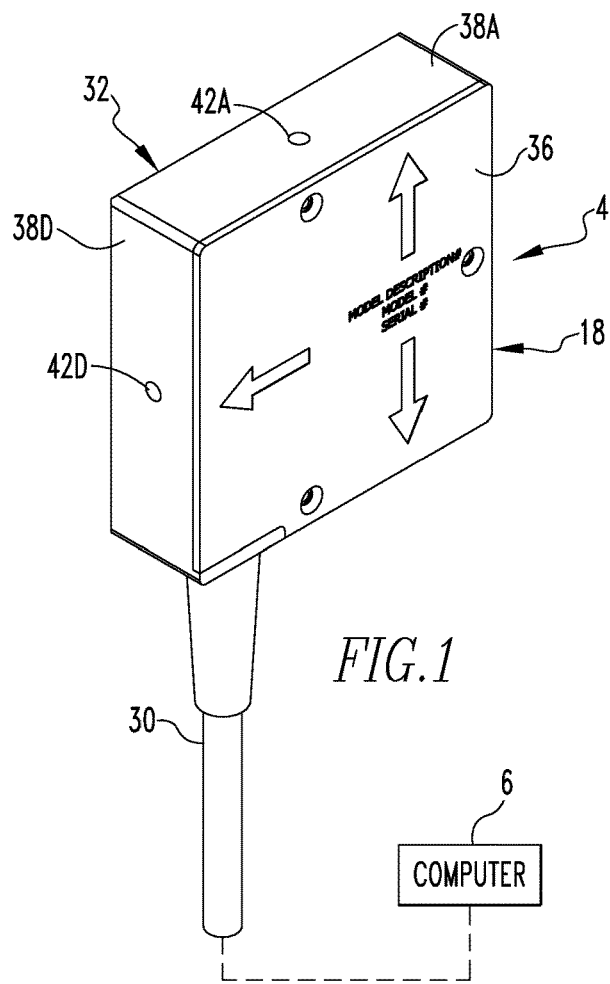
FIG. 1 is a perspective view of an improved phased array transducer apparatus in accordance with the disclosed and claimed concept.

An improved phased array transducer apparatus is indicated herein at the numeral 4 and is variously referred to herein as a "phased array transducer apparatus" and a "transducer apparatus". As can be understood from FIG. 1, the transducer apparatus 4 is connectable with a computer 6 which has an ultrasonic operating system that is executable thereon to cause the computer 6 and the transducer apparatus 4 to perform various operations, including a nondestructive testing operation, as will be set forth in greater detail below. As can be understood from FIG. 7, the transducer apparatus 4 is carried on a schematically-depicted tool 8 into an environment such as a nuclear environment 10 in order to perform a nondestructive ultrasonic (UT) evaluation on a component under test 12. As can be seen in FIG. 7, the component under test 12 includes a weldment 14. The transducer apparatus 4 is depicted in FIG. 7 as being situated on a surface of the component under test 12 in a region adjacent and spaced from the weldment 14 and is thus depicted in FIG. 7 as performing an ultrasonic inspection on the component under test 12 that is situated adjacent the weldment 14. It will be understood that the transducer apparatus 4 is likewise usable to inspect the weldment 14 itself by moving the transducer apparatus 4 closer to the weldment 14.

As can be understood from FIGS. 1-5, the transducer apparatus 4 can be said to include a housing 18 and a detection apparatus 20, with the detection apparatus 20 being situated on the housing 18. The detection apparatus 20 can be said to include six PASAs that are indicated at the numerals 24A, 24B, 24C, 24D, 24E, and 24F, and which can be collectively or individually referred to herein with the numeral 24. Each PASA 24 includes a plurality of Ultrasonic (UT) elements 26 of a type that are generally known in the relevant art.

In the depicted exemplary embodiment each PASA 24 is of an exemplary arrangement of four (4) UT elements 26 along a first axis by five (5) UT elements 26 along a transverse second axis for a total of twenty (20) UT elements 26 for each PASA 24. It is understood, however, that other embodiments the PASAs 24 could have greater or lesser numbers of UT elements 26 along each of the first axis and the second axis without departing from the spirit of the instant disclosure. For instance, the PASAs 24 could instead have two (2), three (3), or five (5) or more UT elements 26 along the first axis. Similarly, and by way of further example, the PASAs 24 could instead have two (2), three (3), four (4), six (6), seven (7), eight (8) or more UT elements 26 along the second axis.

The detection apparatus 20 further includes a cable 30 that is mounted on and that extends from the housing 18 and which carries therein a plurality of individual coaxial cables, with each coaxial cable being connected with an individual corresponding ultrasonic element 26 of one of the PASAs 24. The cable 30 is typically elongated a certain distance, typically long enough to extend out of the nuclear environment 10, and it includes a number of connectors at the end opposite the housing 18 which can connect with and interface with the computer 6.

Figure 2:
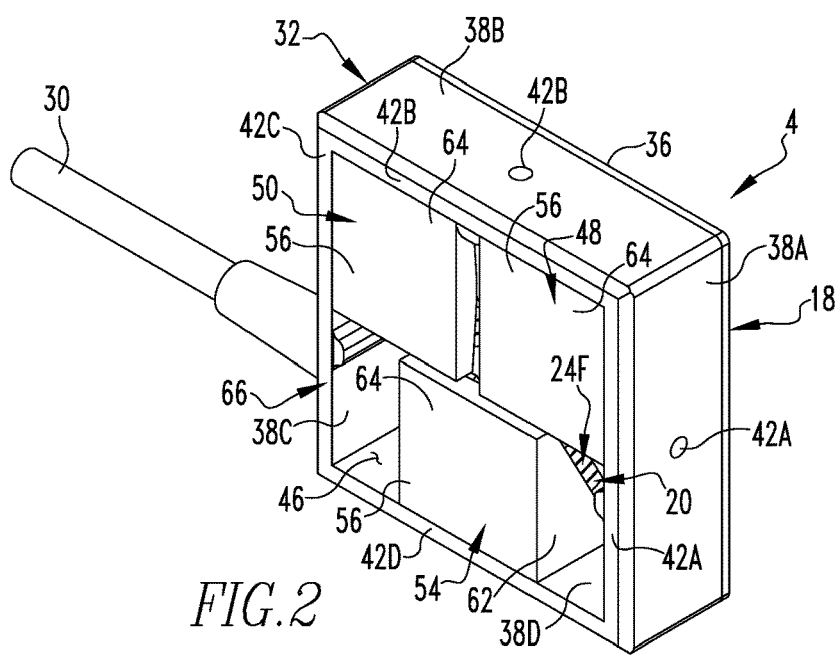
FIG. 2 is another view of the phased array transducer apparatus of FIG. 1, except from a different direction.
Figure 3:
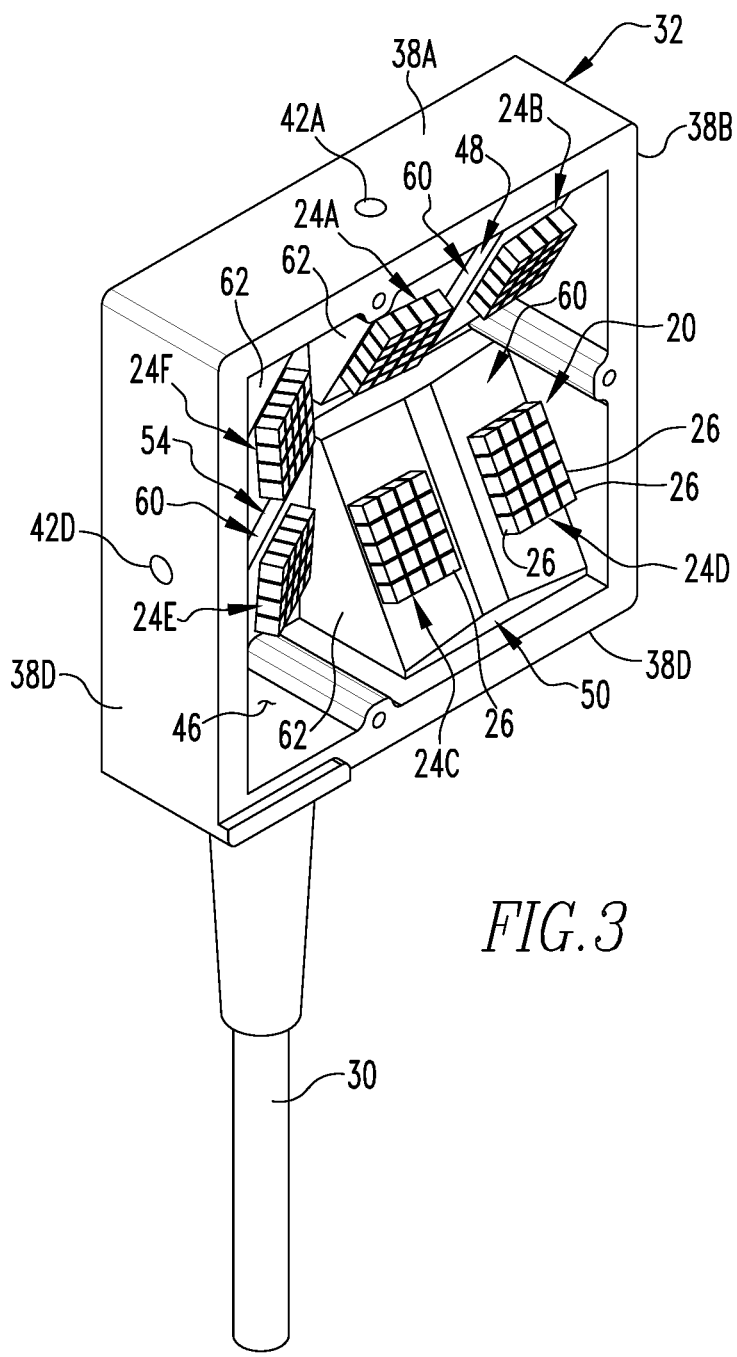
FIG. 3 is a view similar to FIG. 1, except depicting the phased array transducer apparatus with a cover removed from a housing thereof.
Figure 4:
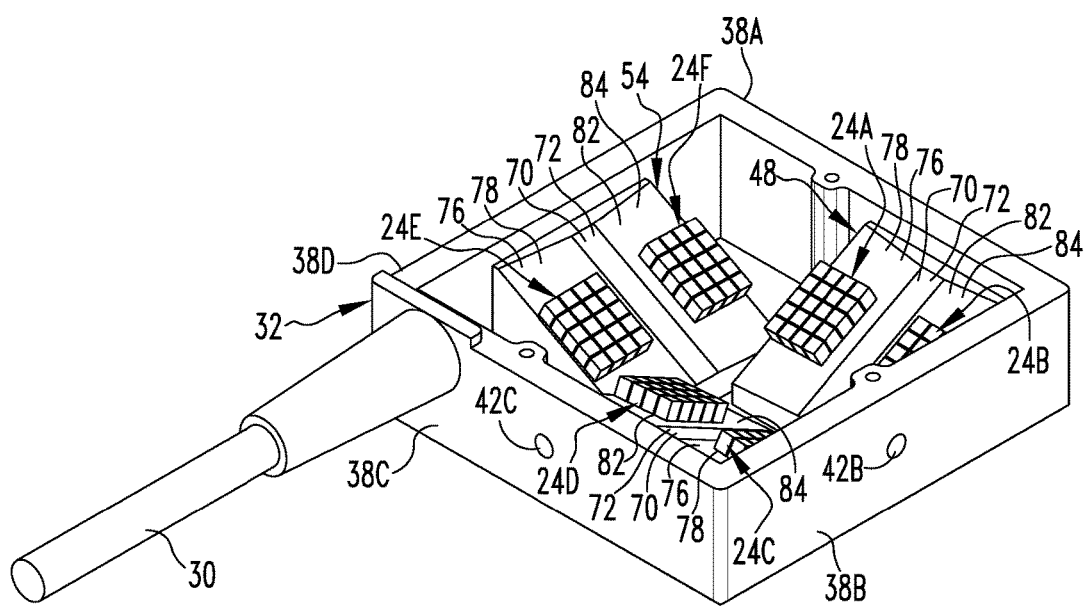
FIG. 4 is a view similar to FIG. 3, except from a different direction.

As can be seen in FIGS. 1-4, the housing 18 can be said to include a base 32 and a cover 36. The cover 36 is depicted in FIGS. 1 and 2 as being situated on the base 32. The base 32 is depicted in FIGS. 3 and 4 as having the cover 36 removed therefrom.

The base 32 can be said to include four sidewalls that are indicated at the numerals 38A, 38B, 38C, and 38D, and which may be collectively or individually referred to herein with the numeral 38. The sidewalls 38 are arranged in a rectangular shape. The housing 18 has formed therein four holes that are indicated at the numerals 42A, 42B, 42C, and 42D, and which may be collectively or individually referred to herein with the numeral 42, that are formed in the sidewalls 38A, 38B, 38C, and 38D, respectively. Furthermore, the sidewalls 38A, 38B, 38C, and 38D can each be said to have an edge surface 44A, 44B, 44C, and 44D, respectively. The edge surfaces 44A, 44B, 44C, and 44D may be collectively or individually referred to herein with the numeral 44. It can be understood that the edge surfaces 44 in the depicted exemplary embodiment are coplanar with one another. The tool 8 is connected with the holes 42 and typically includes a Gimbal device or other such device that enables secure contact between the housing 18 and the component under test 12 during the ultrasonic testing thereof regardless of the contour of the exterior surface of the component under test 12.

The housing 18 can be said to have an interior region 46 that is bounded by an inner surface of the cover 36, the edge surfaces 44, and the inner surface of the sidewalls 38. The housing 18 can further be said to include a plurality of supports that are indicated at the numerals 48, 50, and 54, and which are situated within the interior region 46. The supports 48, 50, and 54 are each of a wedge-like configuration and are each affixed to one or more of the sidewalls 38. The support 48 is affixed to the sidewalls 38A and 38B. The support 50 is affixed to the sidewalls 38B and 38C. The support 52 is affixed to the sidewall 38D.

As can be understood from FIGS. 2-4, each of the supports 48, 50, and 54 includes a lower wall 56, an upper wall 60, and a number of lateral walls 62, with lateral walls 62 each extending between the lower and upper walls 56 and 60. As employed herein, the expression "a number of" and variations thereof shall refer broadly to any non-zero quantity, including a quantity of one. That is, the support 52 includes a pair of the lateral walls 62, whereas the supports 48 and 50 each include only a single lateral wall 62.

The lower walls 56 each include a lower wall surface 64 that is of a generally planar configuration. The lower wall surfaces 64 and the edge surfaces 44 are coplanar with one another and together form an engagement surface 66 that is engageable with the component under test 12 when the ultrasonic testing operation is performed by the transducer apparatus 4.

As can be understood from FIGS. 3 and 4, the upper wall 60 of each of the supports 48, 50, and 54 can be said to include a central portion 70 having a generally planar central surface 72, a first support portion 76 situated adjacent the central portion 70 and having a first support surface 78, and a second support portion 82 situated adjacent the central portion 70 opposite the first support portion 76 and having a second support surface 84. As can be understood from FIG. 6, the upper walls 60 of the supports 48 and 50 can each be said to be oriented at a gross angle 86 with respect to the corresponding lower walls 56, and the gross angle 86 is apparent in FIG. 6 as extending between the lower wall surface 64 of the supports 48 and 50 and the central surface 72 thereof. It is understood that the support 54 has a similar configuration, albeit in a direction orthogonal to the supports 48 and 50. In the depicted exemplary embodiment, the gross angle 86 is twenty-eight degrees, although it is understood that angles lesser than and greater than this amount are possible without departing from the spirit of the instant disclosure. The gross angle 86 thus constitutes an oblique angle since the term "oblique angle" is broadly referred to herein as an angle that is neither parallel nor perpendicular to a reference.

As can be understood from FIGS. 3, 4, and 8, the first support surface 78 is additionally oriented at a first roof angle 88 with respect to the central surface 72 in each of the supports 48, 50, and 54. That is, while the first roof angle 88 is depicted generally FIG. 8 as being between the central surface 72 and the first support surface 78 of the support 54, it can be understood that the same relationship exists in the supports 48 and 50. Likewise in FIG. 8, it can be seen that the second support surface 84 is oriented at a second roof angle 90 with respect to the central surface 72 in each of the supports 48, 50, and 54. In the depicted exemplary embodiment, the first and second roof angles 88 and 90 are approximately 3.5 degrees in magnitude, although angles greater than or lesser than this amount can be employed without departing from the spirit of the instant disclosure.

As can be understood from FIGS. 3, 4, and 8, the first and second roof angles 88 and 90 are of the same magnitude but are in opposite directions with respect to the central surface 72. The first and second roof angles 88 and 90 are likewise oblique angles. Inasmuch as the first and second support surfaces 78 and 80 are oriented with respect to the engagement surface 66 by the first and second roof angles 88 and 90, respectively, as well as the gross angle 86, it can be understood that the first and second support surfaces 78 and 84 can each be said to be oriented at a compound angle with respect to the engagement surface 66, albeit in complementary and opposite directions with respect to the central surface 72.

As can be understood from FIGS. 3 and 4, the PASA 24A is situated on the first support surface 78 of the support 48, and the PASA 24B is situated on the second support surface 84 of the support 48. The PASA 24C is situated on the first support surface 78 of the support 50, and the PASA 24D is situated on the second support surface 84 of the support 50. In a similar fashion, the PASA 24E is situated on the first support surface 78 of the support 54, and the PASA 24F is situated on the second support surface 84 of the support 54. It thus can be seen that the PASAs 24A and 24B are arranged as a pair on the support 48, and in a like fashion the PASAs 24C and 24D are arranged as a pair on the support 50 and the PASAs 24E and 24F are situated as a pair on the support 54. Such pairing of the PASAs 24 enables one of the PASAs 24 in each such pair to operate as a transmission device which outputs ultrasonic signals away from the housing 18 and into the component under test 12 and permits the other PASA 24 of the pair to serve as a receiver which receives reflected ultrasonic signals in order to detect a flaw in the component under test 12.

Figure 5:
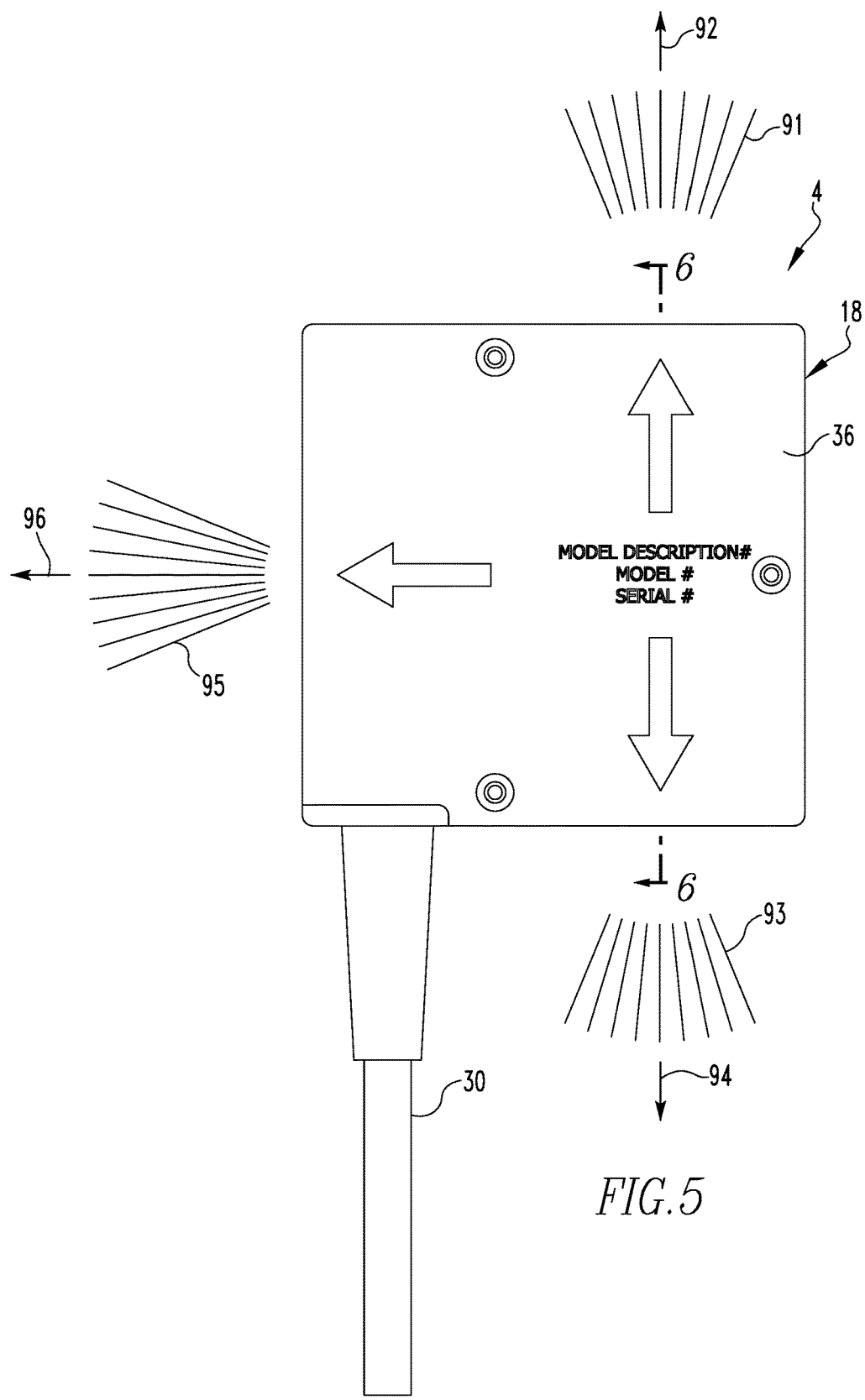
FIG. 5 is a front elevational view of the phased array transducer apparatus of FIG. 1.

As can be understood from FIGS. 5-7, one PASA 24 from among the pair of PASAs 24A and 24B emits a set of first ultrasonic signals 91 that are communicated in generally a first direction 92 away from the housing 18 and into the component under test 12. Likewise, one PASA 24 from among the pair of PASAs 24C and 24D emits a set of second ultrasonic signals 93 that are communicated in a second direction 94 generally away from the housing 18 and into the component under test 12. Similarly, one PASA 24 from among the pair of PASAs 24E and 24F emits a set of third ultrasonic signals 95 that are directed in a third direction 96 generally away from the housing 18 and into the component under test 12. As can be understood from FIGS. 5 and 6, the first and second directions 92 and 94 are generally opposite one another. As can be understood from FIGS. 5 and 7, the third direction 96 is generally perpendicular to the first and second directions 92 and 94. It is understood that the first, second, and third directions 92, 94, and 96 refer generally to the directions within a plane from which the first, second, and third ultrasonic signals 91, 93, and 95 emanate from the PASAs 24 away from the housing 18. In this regard, it is understood from FIGS. 6 and 7 that in addition to the first, second, and third ultrasonic signals 91, 93, and 95 being directed in the first, second, and third directions 92, 94, and 96 away from the housing 18, the first, second, and third ultrasonic signals 91, 93, and 95 are also directed in a direction generally toward the engagement surface 66 and into the component under test 12 wherein the first, second, and third ultrasonic signals 91, 93, and 95 refract. Furthermore, it is understood that the generation of the first, second, and third ultrasonic signals 91, 93, and 95 and whatever steering or orienting of such signals may occur with respect to the housing 18 is driven by the ultrasonic operating system that is executed on the computer 6 and which operates the PASAs 24.

It thus can be seen that the arrangement of the PASAs 24 on the housing 18 results in the generation of ultrasonic testing signals such as the ultrasonic signals 91, 93, and 95 emanating in multiple directions from the housing 18 in order to perform a nondestructive ultrasonic testing operation on the component under test 12. By providing the PASAs 24 oriented at such compound angles with respect to the engagement surface 66 and with respect to the component under test 12, the ultrasonic signals that emanate from the transducer apparatus 4 are sufficiently diversely directed to thoroughly inspect an area of the component under test 12 with a single pass of the transducer apparatus 4 along the area being inspected. The transducer apparatus 4 advantageously need not be removed and repositioned, for instance, with respect to the tool 8 in order to test the same area but in a different direction, for example. This advantageously saves time, effort, and money, which is desirable.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A phased array transducer apparatus structured to be connectable with a computer and to be carried by a tool into a nuclear environment to perform an ultrasonic inspection operation on a component under test within the nuclear environment, the phased array transducer apparatus comprising:
   a housing comprising a base, the base having an engagement surface that is structured to be engaged with the component under test during at least a portion of the ultrasonic inspection operation;
   a plurality of Phased Array SubAssemblies (PASAs) each comprising a plurality of ultrasonic elements and being situated on the base, the plurality of PASAs comprising a first PASA, a second PASA, a third PASA, a fourth PASA, a fifth PASA, and a sixth PASA;
   the first PASA being oriented at a first oblique angle with respect to the engagement surface and being structured to output a first ultrasonic signal into the component under test;
   the second PASA being oriented at a second oblique angle with respect to the engagement surface and being structured to output a second ultrasonic signal into the component under test;
   the third PASA being oriented at a third oblique angle with respect to the engagement surface and being structured to output a third ultrasonic signal into the component under test;
   the fourth PASA being oriented at a fourth oblique angle with respect to the engagement surface, the fourth PASA being structured to receive from the component under test a flaw-based reflection of at least a portion of the first ultrasonic signal and to responsively generate a first output signal that is detectable by the computer;
   the fifth PASA being oriented at a fifth oblique angle with respect to the engagement surface, the fifth PASA being structured to receive from the component under test a flaw-based reflection of at least a portion of the second ultrasonic signal and to responsively generate a second output signal that is detectable by the computer; and
   the sixth PASA being oriented at a sixth oblique angle with respect to the engagement surface, the sixth PASA being structured to receive from the component under test a flaw-based reflection of at least a portion of the third ultrasonic signal and to responsively generate a third output signal that is detectable by the computer.

2. The phased array transducer apparatus of claim 1 wherein the first PASA is positioned on the base to output the first ultrasonic signal in generally a first direction away from the housing and into the component under test, wherein the second PASA is positioned on the base to output the second ultrasonic signal in generally a second direction away from the housing and into the component under test, the first and second directions being substantially opposite one another.

3. The phased array transducer apparatus of claim 2 wherein the third PASA is positioned on the base to output the third ultrasonic signal in generally a third direction away from the housing and into the component under test, the third direction being substantially perpendicular the first and second directions.

4. The phased array transducer apparatus of claim 1 wherein the housing further comprises a plurality of supports comprising a first support, a second support, and a third support that are each wedge-like and situated on the base, the first and fourth PASAs being situated on the first support, the second and fifth PASAs being situated on the second support, and the third and sixth PASAs being situated on the third support.

5. The phased array transducer apparatus of claim 4 wherein the first support, the second support, and the third support each comprise a support portion and another support portion, the support portion having a support surface, the another support portion having another support surface, the first support, the second support, and the third support each being oriented at a gross angle with respect to the engagement surface, each support surface further being oriented at a roof angle away from the gross angle to cause the support surface to be oriented at a first compound angle with respect to the engagement surface, each another support surface further being oriented at another roof angle opposite the roof angle away from the gross angle to cause the support surface to be oriented at a second compound angle with respect to the engagement surface.

6. The phased array transducer apparatus of claim 5 wherein the first PASA is situated on the support surface of the first support, wherein the fourth PASA is situated on the another support surface of the first support, wherein the second PASA is situated on the support surface of the second support, wherein the fifth PASA is situated on the another support surface of the second support, wherein the third PASA is situated on the support surface of the third support, and wherein the sixth PASA is situated on the another support surface of the third support.

* * * * *